US010933021B2

United States Patent
Rhinebarger et al.

(10) Patent No.: US 10,933,021 B2
(45) Date of Patent: *Mar. 2, 2021

(54) COMPOSITIONS OF GALLIUM (III) COMPLEXES FOR ORAL ADMINISTRATION

(71) Applicant: Altum Pharmaceuticals Inc., Vancouver (CA)

(72) Inventors: Rickey Roy Rhinebarger, Chapel Hill, NC (US); Gina G. Stetsko, Vancouver (CA)

(73) Assignee: Altum Pharmaceuticals Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/596,603

(22) Filed: Oct. 8, 2019

(65) Prior Publication Data

US 2020/0038334 A1 Feb. 6, 2020

Related U.S. Application Data

(63) Continuation of application No. 15/893,396, filed on Feb. 9, 2018, now Pat. No. 10,548,849.

(60) Provisional application No. 62/457,712, filed on Feb. 10, 2017.

(51) Int. Cl.
| | | |
|---|---|---|
| *A61K 31/4709* | (2006.01) |
| *A61K 9/28* | (2006.01) |
| *A61K 9/48* | (2006.01) |
| *A61K 9/14* | (2006.01) |

(52) U.S. Cl.
CPC ............ *A61K 9/2866* (2013.01); *A61K 9/284* (2013.01); *A61K 9/2846* (2013.01); *A61K 9/4891* (2013.01); *A61K 31/4709* (2013.01); *A61K 9/146* (2013.01)

(58) Field of Classification Search
CPC ......... A61K 31/4709; A61K 9/28; A61K 9/48
See application file for complete search history.

(56) References Cited

FOREIGN PATENT DOCUMENTS

| WO | 2007/100382 A1 | 9/2007 |
| WO | 2011/100642 A1 | 8/2011 |
| WO | 2011/133826 A2 | 10/2011 |

OTHER PUBLICATIONS

International Search Report and Written Opinion dated Aug. 22, 2019 on PCT/IB2018/000213.
Walker M. Translational Cancer Research GmbH SOP F.1.FFC11 dated Feb. 21, 2003.
Holfheinz R-D, et al. International Journal of Clinical Pharmacology and Therapeutics. Vo. 43, No. 12, 590-591 (2005).
Written opinion and search report dated Jul. 30, 2020 on Singapore application 11201907276T.

*Primary Examiner* — Zohreh A Fay
(74) *Attorney, Agent, or Firm* — Brunet & Co. Ltd.; Robert Brunet; Hans Koenig

(57) ABSTRACT

The present invention relates to dosage forms of gallium complexes suitable for oral delivery and methods of preparation thereof. Such dosage forms are useful for the treatment of diseases, including, but not limited to, cancer.

14 Claims, 3 Drawing Sheets

A = amorphous GaQ3:Eudragit L-100/1:1
B = amorphous GaQ3:Eudragit L-100/1:1 wetted
C = amorphous GaQ3:PVP-K12/ 1:1
D = amorphous GaQ3:HPMCP, H55/ 1:1
E = crystalline GaQ3

A = amorphous GaQ3:Eudragit L-100/1:1
B = amorphous GaQ3:Eudragit L-100/1:1 wetted
C = amorphous GaQ3:Eudragit L-100/1:1 exposed to 75% relative humidity A = 30:70 GaQ3:Eudragit L-100
B = 30:70 GaQ3:Eudragit S-100
C = 30:70 GaQ3:Copovidone
D = 30:70 GaQ3:CAP
E = 30:70 GaQ3:HPMCAS-M
F = 30:70 GaQ3:HPMC-P, grade 55
G = crystalline GaQ3

COMPOSITIONS OF GALLIUM (III) COMPLEXES FOR ORAL ADMINISTRATION

CROSS-REFERENCE TO RELATED APPLICATION

This application is a continuation of U.S. patent application Ser. No. 15/893,396, filed on 9 Feb. 2018, now allowed, which claims the benefit and priority of U.S. Provisional Application No. 62/457,712, filed on 10 Feb. 2017, the entirety of each is hereby incorporated by reference.

FIELD OF THE INVENTION

The invention is in the field of dosage formulations—in particular to formulations of gallium (III) complexes, for oral administration.

BACKGROUND ART

Gallium (III) complexes, specifically tris (8-quinolinolato) gallium (III) (GaQ3) have demonstrated promise as antitumor agents for cancer treatment (see Jakupec, M. A. and Keppler, B. H., *Current Topics in Medicinal Chemistry* (2004) 4, 1575-1583; Bernstein, L. R., *etallotherapeutic Drugs and Metal-Based Diagnostic Agents* (2005) Chapter 14: 259-277; and Jakupec, M. A. and Keppler, B. A., *Metal Ions in Biological Systems* (2004) 425-448.) It is believed that the mechanism of action for these drugs is derived from induction of apoptosis. GaQ3 is a much stronger antitumor agent than simple gallium salts such as gallium nitrate (ca. 3× apoptosis induction). In the NCI 60 tumor panel cell line screen, GaQ3 exhibited a very different pattern of anti-tumor activity compared to gallium nitrate. GaQ3 is active against tumor cell lines resistant to gallium nitrate.

Gallium has been found to have benefits as an anti-inflammatory, for treatment of conditions related to calcium and bone metabolism and for tumor imaging as well as for cancer treatments.

In clinical trials with gallium nitrate, continuous infusion over 5-7 days was required to obtain optimal anti-tumor activity, indicating that a continuous systemic exposure to a certain level of gallium is necessary for efficacy (See Bernstein, 2005, supra). This mode of delivery is inconvenient and not practical. To solve this problem, a more convenient delivery method using oral dosing is proposed as the ideal route of administration to obtain the necessary continuous exposure. Additionally, continuous IV dosing is believed to be due to high serum levels of free gallium ion (the $Ga^{3+}$ cation). This would be unavoidable with gallium salts such as gallium nitrate, but could be avoided with a complexed form of gallium such as GaQ3, provided it is stable in circulation in vivo.

A complexed form of gallium, such as GaQ3, is lipophilic and is more easily incorporated into tissues than gallium ion, improving bioavailability compared to simple gallium salts. Human serum binding studies show that GaQ3 binds very weakly to albumin, but strongly to transferrin (Tf), and is very stable at pH 7.4 in serum. (See Groessel, M. and Hartinger, C. G., *Electrophoresis* (2009) 30, 2720-2727 and Hummer, A. A. et al., *J. Med. Chem.* (2012) 55:5601-5613.)

Two properties of GaQ3 present challenging hurdles with respect to pharmaceutical development of an oral dosage form: very poor aqueous solubility, and lack of stability of the gallium complex in the acidic aqueous conditions in the stomach.

GaQ3 solubility in water is reported to be approximately 18-22 ppm. (See Timerbaev, A. R., *Metallomics* (2009) 1, 193-198.) Solubility is improved in isopropanol, acetone, DMSO and other nonaqueous solvents that are not practical for use in oral dosage forms.

The complexed structure of GaQ3 is disrupted completely at pH values below the pKa of 8-hydroxyquinoline (8-HQ; pKa=5.01). At this or lower pH values, the 8-HQ ligands are re-protonated, releasing the $Ga^{3+}$ cation. This is undesirable because the benefits provided by the ligands (high lipophilicity, protein binding affinity and avoidance of free $Ga^{3+}$ cation) are lost, thereby eliminating the advantegous GaQ3 structure required for successful oral delivery of gallium.

An oral GaQ3 clinical study was conducted in Europe with seven patients who were dosed with enteric coated tablets (See Hofheinz, R.-D., et al, *Int. Journal of Clinical Pharmacology and Therapeutics* (2005) 43:590-591 and Collery, P. et al, *Metal Ions in Biology and Medicine* (2006) 521-524). In this study, the tablet core was a simple conventional formulation comprised of crystalline GaQ3 blended with cornstarch, lactose, polyvinylpyrollidone and magnesium stearate. The pressed tablet cores with dose strengths of 10 mg, 20 mg, and 30 mg were then pan-coated using a combination of Eudragit L and S polymers, plus acetone, isopropanol, triacetin and coloring agents for dosage strength differentiation. No attempt was made to reduce the particle size or crystalline nature of the GaQ3 beyond what was derived from the chemical synthesis of the compound (average particle size ca. 10 to 20 μm). While the results from this study indicated that the drug was well tolerated, confirmation of linear pharmacokinetics was not possible and an explicit dose recommendation for further study was not identified (See Timerbaev, 2009, supra). Although an attempt was made to inhibit the loss of the ligand structure using an enteric coating, it was postulated that a significant amount of the drug was not absorbed, thus dramatically limiting bioavailability.

The results from this first clinical evaluation of GaQ3 suggested that the low solubility of the crystalline compound possessing a particle size range normally considered adequate for a conventional formulation resulted in poor bioavailability and non-linear pharmacokinetics. The data indicated that although a portion of GaQ3 survived intact after transit through the stomach, the absorption observed was somewhat erratic through the intestine.

Thus, the challenge in the advancement of oral GaQ3 in clinical development is keeping the GaQ3 intact during transit through the stomach and releasing a more soluble form of GaQ3 within the intestinal tract where the compound is stable and can be absorbed intact.

This challenge is met by: 1) formation of a non-crystalline solid form of GaQ3 and 2) using an enteric coating on the final dosage form or subunits within the final form to prevent exposure to the destabilizing effects of gastric acid.

DISCLOSURE OF THE INVENTION

Thus, in one aspect, the invention is directed to a dosage form for oral administration of GaQ3 or a derivative thereof which comprises an amorphous or nanocrystalline form of said GaQ3 or a derivative thereof protected by an enteric or delayed release coating. In some embodiments, the GaQ3 or its derivative is admixed with a dispersant to maintain its amorphous or nanocrystalline form.

The formulations of the invention result in desirable pharmacokinetics wherein when said encapsulated GaQ3 is administered to dogs at a dose of 10 mg/kg the Cmax in plasma is at least 100 times the Cmax in plasma of dogs administered 10 mg/kg of crystalline GaQ3 and the AUC in plasma is at least 200 times that of dogs administered comparable amounts of crystalline GaQ3. The formulations also have desirable solubility and in the case of amorphous forms, resistance to conversion back to a crystalline state under stress or exposure to moisture.

The invention also includes methods to administer GaQ3 or its derivative utilizing the formulations of the invention. Such formulations are useful in treating cancer and conditions associated with calcium and bone metabolism.

MODES OF CARRYING OUT THE INVENTION

Figure 1:
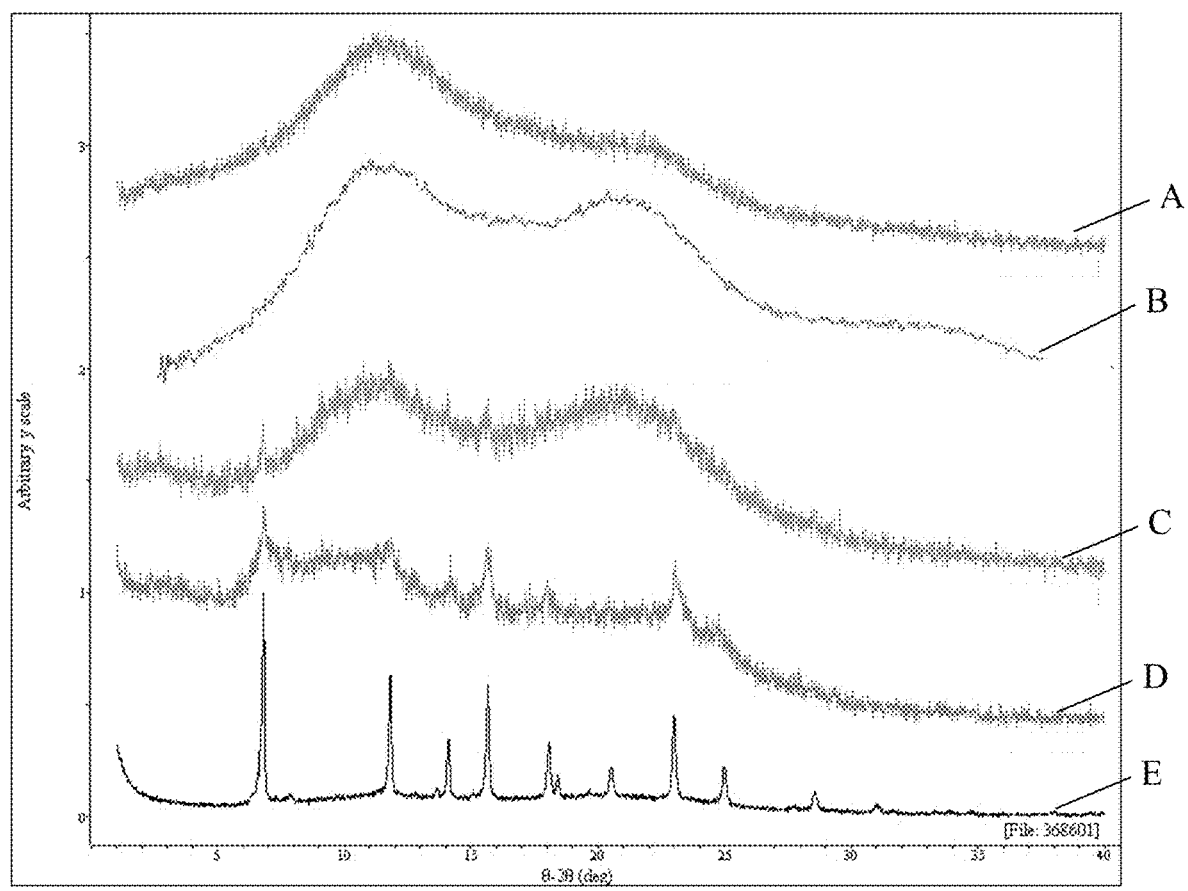
FIG. 1 shows XRD curves for crystalline GaQ3 and amorphous GaQ3 dispersions.

"GaQ3" refers to tris (8-quinolinolato) gallium (III), as shown in Formula 1 and also includes derivatives as described in Formula 2.

Formula 1

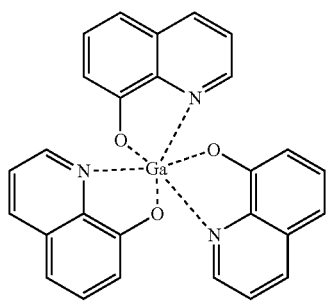

Derivatives of tris (8-quinolinolato) gallium (III), includes those of Formula 2.

Formula 2

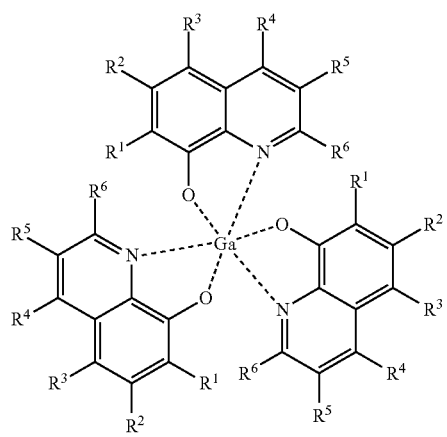

wherein:
each of $R^1$, $R^2$, $R^3$, $R^4$, $R^5$, and $R^6$ are independently selected from hydrogen, fluorine, chlorine, bromine, iodine, $SO_3M$; saturated or unsaturated, straight or branched $C_{1-12}$ hydrocarbon chain, wherein 0-6 methylene units are independently replaced by —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—;

wherein:
M is an alkali metal.
Typically 5 of each $R^1$, $R^2$, $R^3$, $R^4$, $R^5$, and $R^6$ are H and the remaining R in each set is halo or a saturated or unsaturated, straight or branched $C_{1-12}$ hydrocarbon chain, wherein 0-6 methylene units are independently replaced by —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—.

Pharmaceutically acceptable salts are included of those compounds of the invention that are suitable for formation of such salts. For example, where one or more of $R^1$-$R^6$ comprises —NH— this may be in the form of an acid addition salt including those derived from pharmaceutically acceptable inorganic and organic acids.

"GaQ3," as used herein includes derivatives as set forth in formula 2.

Solubility of the GaQ3 is enhanced by converting crystalline GaQ3 to amorphous or nanocrystalline form. Since there is no crystal lattice in the amorphous form, dissolution of the solid is improved from a crystalline form. The amorphous state represents a complete loss of short and long range crystalline order and the energy required for a molecule of drug to dissolve in the gastrointestinal tract is much lower, resulting in a better rate and extent of absorption. The amorphous form or dispersion thereof may be prepared by spray drying, hot melt extrusion, rotary evaporation, freeze-drying or supercritical fluid processing.

An alternative to a completely amorphous state is a nanocrystalline form wherein, similarly, the crystalline lattice energy state is reduced, in this case, through a dramatically increased surface area. Particle size reduction of crystalline drugs to enhance solubility (or dissolution) can be pursued by various well-known mechanical and chemical means. Typical methods involve, chemical, mechanical grinding (wet milling), microfluidization, supercritical fluid processing, spray drying and precipitation techniques. A mean particle size of less than about 400 nanometers (nm) is typically required for enhancement of the solubility (U.S. Pat. No. 5,145,684), but the size range in the composition may be 80 nm-500 nm, or 100 nm-300 nm including intermediate values. The size distribution need not be uniform.

Thus, an alternate method of increasing dissolution of the GaQ3 is to produce crystalline particles with a mean particle size of less than 500 nm, i.e., said nanocrystals. This can be achieved using a wet milling to grind the GaQ3 crystalline size into this size range with the aid of a surface modifier to help maintain discrete particles during and after the milling process. A nanoparticulate dispersion of GaQ3 can be prepared using a DYNO-MILL (Model KDL, manufactured by Willy A. Bachoffen AG Maschinenfabrik).

The surface modifier can be mixed with high purity water in a quantity sufficient to fill the mill. Dry powdered GaQ3 (preferably air jet milled or micronized, average particle size 1-10 um) can be added to the above solution and rolled on a roller mill for one week. This step ensures an even dispersion of the GaQ3 in the surface modifier solution, thereby reducing the treatment time required in the media mill.

This premix can then be added to a holding vessel and agitated with a conventional propeller mixer at low speed to maintain a homogeneous mixture for the media milling process. The mill grinding chamber can be partially filled with silica glass spheres and the premix can be continuously recirculated through the media mill.

In general, the crystalline drug is advantageously processed to convert it to the amorphous or nanocrystalline state in the presence of dispersants. The formulations of the invention thus provide a way to maintain this amorphous or nanoparticulate state in a dosage form during storage and ensure that the release of GaQ3 occurs in a controlled manner for good absorption. A "dispersing agent" or "dispersant", such as a miscible polymer can be used to inhibit crystallization, thereby yielding a long lasting non-crystalline solid state (See Chiou, W. L. and Riegelman, S., *J. Pharm. Sci.* (1971) 60, 1281-1302 and Yu, L., *Adv. Drug Delivery Rev.*, (2001) 48, 27-42).

The dispersed or simply amorphous or nanocrystalline GaQ3 exhibits an instantaneous burst of solubility when mixed with aqueous medium, thus exhibiting an initial peak concentration.

Suitable dispersants include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene caster oil derivatives, polyoxyethylene sorbitan fatty acid esters, polyethyleneglycols, methacrylic acid:methacrylate copolymers, aminoalkyl methacrylate copolymers, polyoxyethylene stearates, colloidol silicon dioxide, phosphates, sodium dodecyl sulfate, carboxy methylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone.

In addition to preventing GaQ3 from reverting to a crystalline state, it is also necessary to prevent the acid conditions in the stomach from dissociating the complex, i.e. to prevent chemical degradation of the GaQ3 complex after oral administration. The use of an enteric or delayed release coating can provide safe passage through the low pH environment of the stomach delaying dissolution until the higher pH of the small intestine is reached. Therefore, formulations of the invention use a protective coating for the amorphous or nanoparticulate GaQ3.

A dissolution control test was established to verify that the desired oral formulation retains its integrity in a simulated gastric environment (stage 1), and then fully releases the GaQ3 in the simulated intestinal environment (stage 2).

Various materials are available in the art to provide the enteric or delayed release coating. These include shellac (esters of aleurtic acid), cellulose acetate phthalate (CAP), poly(methacrylic acid-co-methyl methacrylate), cellulose acetate trimellitate (CAT), poly(vinyl acetate phthalate) (PVAP), and hydroxypropyl methylcellulose phthalate (HPMCP), as well as plant fibers and plastics. (See, e.g., Hussan, S. D. et al., 105 *IOSRJ Pharm* (2012) 2:5-11.) Such coatings may also include hydroxypropylmethylcellulose, hydroxypropylcellulose, aminoalkyl methacrylate copolymers (Eudragit E30D), methacrylic acid:methacrylate copolymers, Eudragit L-100, triacetin, triethylcitrate, polyols such as glycerol, propylene glycol, polyethylene glycols PEG (generally the 200-6000 grades) or organic esters such as phthalate esters (diethyl, dibutyl), citrate esters (triethyl, acetyl triethyl, acetyl tributyl), and oils/glycerides such as castor oil, acetylated monoglycerides and fractionated coconut oil.

The term "pharmaceutically acceptable carrier, adjuvant, or vehicle" refers to a non-toxic carrier, adjuvant, or vehicle that does not destroy the pharmacological activity of the compound with which it is formulated. These may also be included in the formulation.

Pharmaceutically acceptable carriers, adjuvants or vehicles that may also be used in the compositions include, but are not limited to, include: lactose, spray dried lactose, microcrystalline cellulose sorbitol, dibasic calcium phosphate dehydrate, calcium sulphate dihydrate, gelatin, glucose, cellulose derivatives-methyl cellulose, ethyl cellulose, hydroxy propylmethyl cellulose, hydroxy propyl cellulose, starch, polyvinylpyrrolidone (Povidone), sodium alginate, carboxymethylcellulose, acacia, stearic acid, magnesium stearate, calcium stearate, talc, paraffin, sodium lauryl sulphate, sodium benzoate, PEG 400, 600,8000, colloidal silicon dioxide (Aerosil), and cornstarch.

The compositions of the invention are formulated for oral administration to a subject. The compositions may be constructed into dosage forms in a variety of ways. The physical form of the composition may vary—it may be a single coated tablet, a suspension of coated micro particles, a capsule containing a multiplicity of coated mini tablets or micro particles, etc. One embodiment provides an enterically coated tablet or capsule containing GaQ3, wherein the GaQ3 is in an amorphous (non-crystalline) state with commonly used pharmaceutical excipients. Another embodiment provides an enterically coated capsule containing GaQ3, wherein the GaQ3 is in an amorphous state in a powder formulation. Another embodiement provides an enterically coated unit dosage form (tablet or capsule) containing GaQ3, wherein the GaQ3 is in an amorphous or nanocrystalline state. Another embodiment of the present invention provides a capsule filled with coated microparticles that contain amorphous or nanocrystalline GaQ3. Inert spherical microparticles (cellulose or sugar) can be coated with the powdered amorphous or nanocrystalline GaQ3 using a binder solution and subsequently overcoated with an enteric or delayed release polymer coating. Another embodiment provides a capsule filled with coated mini-tablets. The mini-tablets contain the amorphous or nanocrystalline GaQ3 with other excipients that are compressed into tiny tablets that are subsequently coated with an enteric or a delayed release polymer coating prior to filling into a capsule.

In more detail, a nanocrystalline or amorphous suspension can then be transformed into a solid dosage form for oral administration by spraying the nanocrystal suspension on to cellulose or sugar spheres using a fluid bed coater, such as a Glatt GPCG-2. This equipment provides the capability of evaporating the vehicle of the nanocrystal or amorphous suspension, thereby depositing the nanocrystals or the amorphous powder on the surface of the spheres. These spheres can then be overcoated with a subcoat and delayed or enteric polymer coating and the final particles can subsequently filled into capsules. One variant of this approach is to add other materials to the nanocrystalline or powder suspension prior to spraying it, such as polymers, surfactants and/or binding agents.

A liquid dosage form, such as an aqueous suspension is possible by combining final coated particles, described above, with typical excipients in a powder form used for an aqueous suspension formulations and placing the mixture in a bottle for subsequent reconstitution using a prescribed amount of purified water.

Another approach is to prepare multiple mini-tablets that are then coated with enteric or delayed coating prior to filling into a capsule shell. Alternatively, the coated particles can be incorporated in a "fast melt" orally dissolving tablet for rapid dissolution on the tongue.

Another approach is to blend solid particles of amorphous or nanocrystalline GaQ3 into a non-aqueous vehicle, such as vegetable oil or polyethylene glycol and then filling that blend into capsule shells that are then coated with enteric or delayed coating.

The amorphous powder or nanoparticles formed can be sprayed on to typical pharmaceutical adjuvants or microparticles or incorporated in tablet formulations in a manner similar to the formulations described above for the amorphous drug form, for the preparation of tablets, capsules or aqueous suspensions.

In specific illustrative embodiments within the scope of the invention, several polymers were evaluated to prevent crystallization including cellulose acetate phthalate (CAP), copovidone or polyvinylpyrrolidone (Plasdone S-360) and Eudragit L-100 (copolymer of methacrylic acid and methyl acrylate:poly(methylacrylic acid-co-methyl methacrylate1:1). Different experiments examined the induction and maintenance of amorphous character enhanced (initial and long term) solubility after a challenge with sustained exposure to heat and high relative humidity stress conditions. The results of these experiments indicated good results for Eudragit L-100.

Thus, certain embodiments, the present invention provides an amorphous dispersion of GaQ3 in a polymer matrix, wherein the polymer matrix is Eudragit L-100. In other embodiments, the polymer matrix is selected from CAP, copovidone, a Eudragit variant or other polymers or materials.

In certain embodiments, the present invention provides an amorphous dispersion of GaQ3 in a polymer matrix, wherein the GaQ3:polymer weight ratio is between 1:9 and 9:1. In other embodiments, the weight ratio is 7:3, 3:2, 5:5, 2:3 or 3:7. In other embodiments, the amorphous dispersion is comprised of 40% GaQ3 and 60% Eudragit L-100 wt/wt. In yet another embodiment, the amorphous dispersion contains between 30 to 60% GaQ3 and 40 to 70% Eudragit L-100 all wt/wt.

An enteric-coated tablet formulation was prepared as a prototype product for further evaluation using a GaQ3:Eudragit L-100 dispersion ratio of 40:60 wt/wt was utilized.

Microcrystalline cellulose was included in the formulation as filler and bulking agent since it is insoluble but swells in water and helps to give shape and physical stability to the compressed tablet and has high compressibility and inherent lubricity. Polyvinylpyrrolidone was included in the formulation as a binder and solubility enhancer. Croscarmellose Sodium (internally cross-linked sodium carboxymethylcellulose) was included in the formulation as a disintegrant. Silicon dioxide was included in the formulation as a flow aid and to improve the processing of the powdered formulation after roller compaction, and to improve powder flowability in the hopper during tableting. Magnesium stearate was included in the formulation as a lubricant and prevents sticking of the the formulation to the contact surfaces of the tableting press during tablet compression. Advantia Prime and Advantia Performance are proprietary pharmaceutical coating formulations manufactured by the ISP Corporation and these materials were used to provide primary subcoating and secondary enteric coat on the finished tablets, respectively.

Alternatively, spray dried amorphous powder or nanoparticles of a selected drug/polymer ratio are sprayed on to small spheres made of cellulose (Cellets™) or sugar spheres using fluid bed coating equipment such as a Glatt GPCG-2 or larger. In another embodiment the liquid dispersion of GaQ3/Eudragit L-100 is sprayed directly onto the small spheres forming an amorphous layer of the dispersion.

The drug-layered spheres are then overcoated with a subcoat and an enteric coating or just an enteric coating (Eudragit L-100) or with a delayed release coating. The coated beads can then filled into a capsule shell.

The term "subject", as used herein, means an animal, e.g., a mammal or specifically a human. The animal may be a laboratory model for a disease to be treated, such as a rat or mouse.

The pharmaceutically acceptable compositions of this invention are orally administered to a subject in any orally acceptable dosage form including, but not limited to, capsules, tablets, encapsulated coated mini-tablets, encapsulated coated microparticles, suspensions of coated microparticles and coated liquid capsules filled with non-aqueous suspension of GaQ3. In the case of tablets or mini-tablets for oral use, carriers commonly used include lactose and other fillers, such as microcrystalline cellulose and corn starch. Lubricating agents, such as magnesium stearate, are also typically added. For oral administration in a capsule form, useful diluents include lactose and other fillers, such as, microcrystalline cellulose dried cornstarch, lubricating and flow agents, such as, magnesium stearate and silicon dioxide. For microparticles in capsules, sugar or cellulose spheres, and binding agents such as polyvinylpyrolidone or hydroxypropylmethylcellulose provide the formulation.

When aqueous suspensions are required for oral use, microparticles containing amorphous or nanocrystalline active ingredient may be incorporated in or on the microparticles and then combined with emulsifying and suspending agents in a powdered form for subsequent reconstitution with purified water prior to administration. If desired, certain sweetening, flavoring or coloring agents may also be added. In certain embodiments, pharmaceutically acceptable compositions of the present invention are enterically coated and/or coated with polymers that delay the release in the gastrointestinal tract.

For oral liquid products, pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

The amount of the active compound of the present invention that may be combined with the carrier materials to produce a composition in a dosage form will vary depending upon the host treated and the particular mode of administration. Preferably, the compositions should be formulated so that a drug dosage of between 0.01-100-mg/kg body weight/day can be administered to a subject.

It should also be understood that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease being treated. The amount of an active compound of the present invention in the composition will also depend upon the particular active compound in the composition.

As noted above, the subject to whom the formulation is to be administered typically is subject to a condition such as cancer, inflammation, or a condition of calcium or bone metabolism that is undesirable. The invention, however, resides in the successful formulation of complexes of gallium—i.e., GaQ3 including its derivatives so that bioavailability is assured by the combination of an enteric or delayed release coating that prevents premature dissolution or degradation of the complex in the acid environment of the stomach, and the successful enhancement of solubility of the active compound by providing an amorphous or nanoparticulate form that can be preserved by providing a suitable dispersant.

The compositions of the invention are also characterized by their ability to provide favorable pharmacokinetics. A model in dogs has been tested which has established the abilities of the claimed formulations to provide favorable maximum concentration (Cmax) and area under the curve (AUC) results in plasma. Specifically, it has been shown that the compositions of the invention provide a Cmax in plasma that is at least 100 times a Cmax in plasma when crystalline GaQ3 is administered orally. The superior effects of the composition on Cmax may also be such that they exhibit a Cmax at least 50 times that of crystalline GaQ3, or at least 20 times the Cmax of crystalline GaQ3, or 10 times the Cmax of crystalline GaQ3.

Similarly, the compositions of the invention will provide an AUC in plasma at least 200 times the AUC in plasma of subjects administered the same amount of crystalline GaQ3, or at least 100 times, or at least 50 times, or at least 20 times, or at least 10 times of the AUC in plasma compared to that provided by a similar amount of crystalline GaQ3.

As shown in the Examples below, values of Cmax and AUC have been established in male and female dogs. The formulations of the invention exhibit Cmax and AUC in dogs "equivalent" to those described—i.e., within 80%-125% of these values. "Equivalent", as used herein is defined as within 80%-125% of the referent.

EXAMPLES

The following examples are for illustration and do not limit the invention.

Example 1

Formation of Dispersed Amorphous GaQ3

Various dispersing agents of rotary evaporation and spray drying (SDD) were employed using:
hydroxypropylmethylcellulose-acetate succinate, (grade HG);
hydroxypropylmethylcellulose phthalate, (grade 55);
polyvinylpyrrolidone, (grades K-12, K-29/32 and K-90); and
Eudragit L-100

These were supplied as 1:1 GaQ3:polymer weight ratios. Eudragit L-100 was further evaluated at ~1:2 and ~1:3 weight ratios.

In more detail these spray-dried dispersions were prepared with a two-fluid approach, wherein the GaQ3 was pre-dissolved in dichloromethane and Eudragit L-100 pre-dissolved in methanol. Spray rates were adjusted to afford the 1:1 weight ratio of GaQ3 to the polymeric dispersing agent, and the resulting product dried under vacuum. This was performed initially at a 1.7 gram pilot scale, and then at ~4.2 and 5.2 gram scales. These results were sufficient to engage in further SDD scale-up, followed by final drug product formulation development. Spray dried dispersions were prepared using a GEA-Niro SD Micro™ Spray Dryer at a ratio of 30:70 (wt/wt) GaQ3 to dispersant. After drying, all samples were tested in triplicate for non-sink kinetic solubility in a simulated intestinal fluid solution.

Analytical techniques used for evaluation included hot stage (HSM) and polarized light microscopies (PLM), Xray powder diffraction (XRPD), differential scanning calorimetry (DSC) and modulated DSC, and thermogravimetric analysis with infrared (TGA-IR). XRPD (observation of the broad amorphous halo effect vs. sharply defined reflections at specific 2θ values) and PLM (absence of particle birefringence consistent with amorphous character) were the most useful methods to ascertain achievement and retention of the amorphous state for all mixtures prepared and tested. XRPD of various GaQ3 and dispersant mixtures are shown in FIG. 1.

Figure 2:
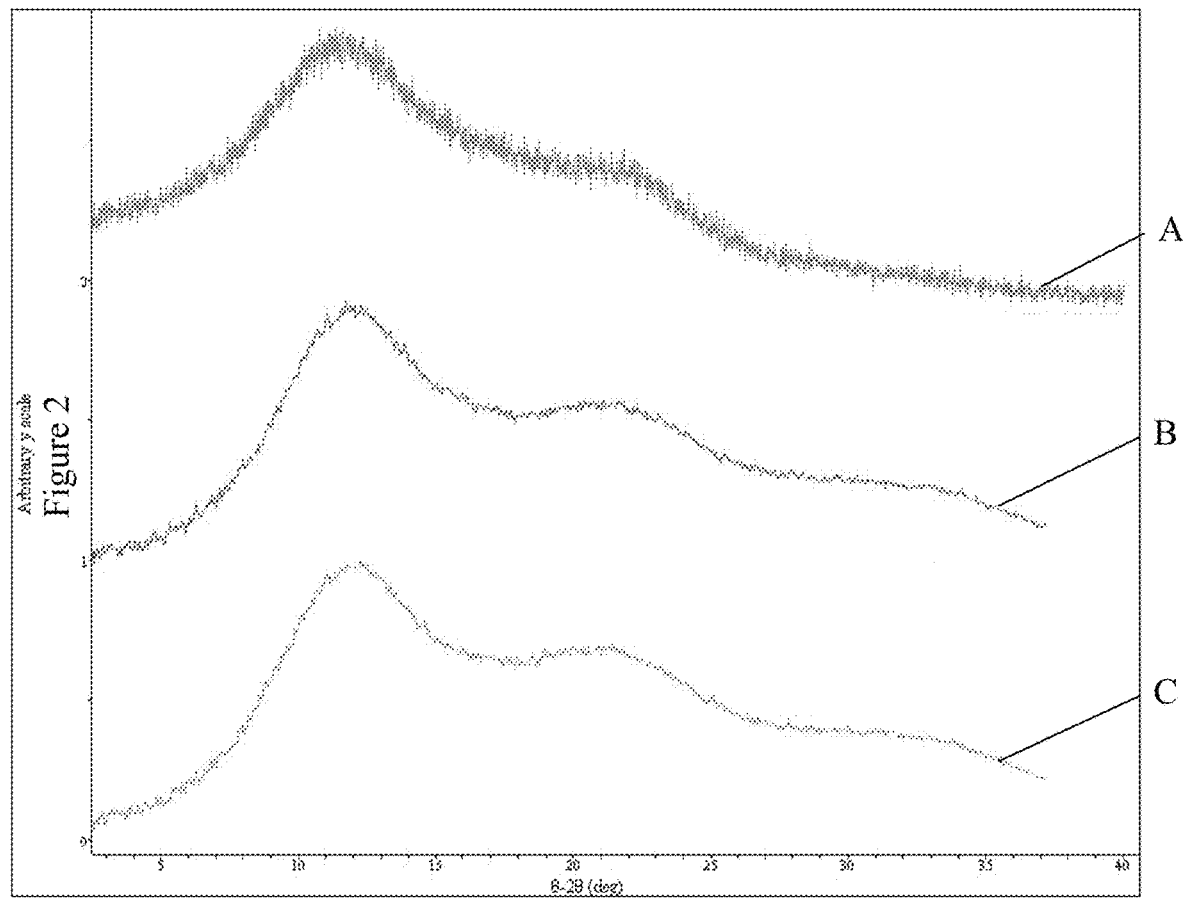
FIG. 2 shows retention of amorphous state of GaQ3 in a 1:1 dispersion with Eudragit L-100 when exposed to water.

As shown most dispersants maintain GaQ3 in an amorphous state. FIG. 1 shows a dispersion with Eudragit L-100 which in particular shows clear retention of the amorphous state. In addition, samples of the 1:1 GaQ3/Eudragit L-100 dispersion subjected to water, USP simulated gastric fluid (SGF) and USP simulated intestinal fluid (SIF); (slurried for 24 hr) showed no apparent evidence of crystallization. This resistance is shown in more detail in FIG. 2.

A drug loading optimization study was also conducted by adjusting the liquid feed rate of the GaQ3 and Eudragit stock solutions in spray dried dispersions prepared at 35:65, 40:60, 50:50, and 60:40 (wt/wt) GaQ3:Eudragit L-100 ratios. Samples were vacuum dried for five days at 45° C. to 55° C., then analyzed by visual appearance, identification, assay and purity by HPLC, Karl Fischer moisture, XRPD and PLM. Stability testing was conducted at one month at 25° C./60% R.H. and 40° C./75% R.H. for one week and one month. PLM revealed some birefringence for the 60:40 GaQ3/Eudragit L-100 dispersion, but all XRPD results indicated predominantly amorphous character. This finding indicates that Eudragit L-100 at the 60:40 ratio blocked restoration of the crystalline form. More detailed investigation using PLM indicated the characterization as "amorphous".

Example 2

Preparation of Enteric Coated Tablets

Engineering batches of 4 mg and 20 mg tablets were prepared. Tablet enteric coating was performed on both 4 mg and 20 mg tablet cores using an O'Hara Labcoat I system with a 15" coating pan. Initial tablet testing included appearance, water content, dissolution, HPLC assay and purity. These trial examples compared the use of either Advantia™ Preferred HS or Advantia™ Prime components as the base coat (3% w/w applied as aqueous suspensions), followed by final coating with Advantia™ Performance Coating (10% w/w aqueous suspension) to provide the enteric protection for both dosing strengths. Stability testing was conducted on all four tablet lots at 25° C./60% R.H. and 40° C./75% R.H. conditions for one and three months. It was concluded that the Advantia™ Prime subcoat provided a perceived advantage and was selected over Advantia™ Preferred HS. The compositions of the tablets is shown in Table 1.

TABLE 1

Formulas for 4 mg and 20 mg GaQ3 Enteric Coated Tablets.

| Component | 4 mg Dose | | 20 mg Dose | |
|---|---|---|---|---|
| | mg | % | mg | % |
| GaQ3 Drug Substance | 4.0 | 2.0 | 20 | 10.0 |
| Eudragit L-100 | 6.0 | 3.0 | 30 | 15.0 |
| Microcrystalline Cellulose, NF | 178.0 | 89.0 | 138.0 | 69.0 |
| Polyvinylpyrrolidone, NF | 4.0 | 2.0 | 4.0 | 2.0 |
| Croscarmellose Sodium, NF | 6.0 | 3.0 | 6.0 | 3.0 |
| Silicon Dioxide, NF | 1.0 | 0.5 | 1.0 | 0.5 |
| Magnesium Stearate, NF | 1.0 | 0.5 | 1.0 | 0.5 |
| Tablet Core | 200.0 | 100.0 | 200.0 | 100.0 |
| Advantia Prime* | 6.0 | | 6.0 | |
| Advantia Performance White** | 21.0 | | — | |
| Advantia Performance Yellow** | — | | 21.0 | |
| Total Tablet Weight | 227.0 | | 227.0 | |

*water soluble cellulose based coating,
**acrylic based enteric polymer

Example 3

Pharmacokinetics in Dogs

Oral pharmacokinetics were studied in dogs to compare the bioavailablity of unmodified crystalline GaQ3 with an amorphous polymer dispersion of GaQ3 in an enteric coated capsule. Unmodified crystalline GaQ3 in gelatin capsules was compared with GaQ3 amorphous dispersion (spray dried dispersion of 30% GaQ3 and 70% Eudragit L-100) in gelatin capsules enteric coated with Eudragit L-100 polymer. Capsules were administered to dogs at a dose of 10 mg/kg GaQ3, and plasma was collected pre-dose, 0.5, 1, 3, 5, 8, 24, 48, and 72 hours. GaQ3 concentrations in the plasma were quantified by ICP-MS.

For the unmodified crystalline drug, the $C_{Max}$ (maximum concentration) of GaQ3 in the plasma was 16.1 ng/mL at 3 hours. For the amorphous dispersion, the $C_{Max}$ of GaQ3 in the plasma was 2,335.6 ng/mL at 3 hours. This represents a 145-fold increase in $C_{Max}$ for the amorphous dispersion when compared to the unmodified crystalline drug. For the unmodified crystalline drug, the AUC (area under the curve) of GaQ3 in the plasma was 213.8 ng*h/mL and for the amorphous dispersion, the AUC of GaQ3 in the plasma was 60,546 ng*h/mL. This represents a 283-fold increase in AUC for the amorphous dispersion when compared to the unmodified crystalline drug.

Example 4

28 Day Dog Study

Doses of a 40:60 GaQ3:Eudragit L-100 powder were filled into gelatin capsules that were dip coated in a solution opf Eudragit L-100 polymer and triethyl citrate (plasticizer). The coated capsules were administered to groups of male and female dogs in the fasted state.

Blood samples were collected from all animals, pre-dose, and at 30 minutes and 1, 3, 5, 8, 24 hours after dosing on Days 1 and 28.

A summary of the toxicokinetic/pharmacokinetic parameters is shown in Table 2.

TABLE 2

| Group | Dose (mg/m²) | Dose (mg/kg) | $T_{max}$ (h) | $C_{max}$ (ng/mL) | $T_{last}$ (h) | $AUC_{last}$ (h * ng/mL) | $AUC_{0-24}$ (h * ng/mL) |
|---|---|---|---|---|---|---|---|
| Day 1, Females | | | | | | | |
| 2 | 2.5 | 0.125 | 3.0 | 36.73 | 24 | 492.6 | 492.6 |
| 3 | 10 | 0.5 | 3.7 | 199.70 | 24 | 2825.2 | 2825.2 |
| 4 | 20 | 1.0 | 4.4 | 329.38 | 24 | 4380.9 | 4380.9 |
| Day 1, Males | | | | | | | |
| 2 | 2.5 | 0.125 | 2.3 | 24.53 | 13 | 232.0 | 451.1 |
| 3 | 10 | 0.5 | 3.0 | 123.33 | 24 | 1536.4 | 1536.4 |
| 4 | 20 | 1.0 | 3.4 | 309.61 | 24 | 4227.4 | 4227.4 |
| Day 28, Females | | | | | | | |
| 2 | 2.5 | 0.125 | 3.0 | 36.09 | 24 | 579.5 | 579.5 |
| 3 | 10 | 0.5 | 2.3 | 288.48 | 24 | 4540.8 | 4540.8 |
| 4 | 20 | 1.0 | 2.6 | 496.78 | 43 | 9572.6 | 7551.8 |
| Day 28, Males | | | | | | | |
| 2 | 2.5 | 0.125 | 2.3 | 38.07 | 24 | 567.5 | 567.5 |
| 3 | 10 | 0.5 | 3.0 | 271.66 | 24 | 3871.4 | 3871.4 |
| 4 | 20 | 1.0 | 3.0 | 494.69 | 43 | 9398.3 | 7516.0 |

Example 5

Dissolution Kinetics

Figure 3:
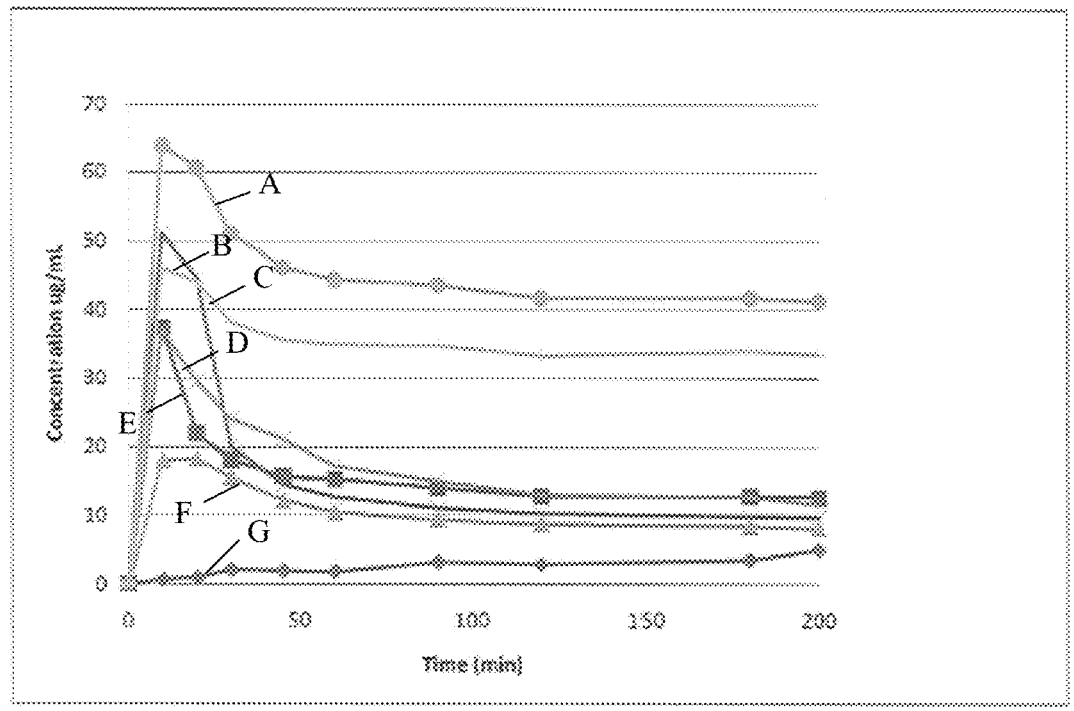
FIG. 3 shows the kinetics of dissolution for various dispersions of GaQ3 as compared to crystalline GaQ3.

The kinetics of solution of crystalline GaQ3 were compared with those of amorphous GaQ3 dispersed in various dispersants by measuring the concentration of GaQ3 in water as a function of time for dispersions of amorphous GaQ3:dispersant/30:70. The results are shown in FIG. 3. As shown, more immediate peak of dissolution was obtained with initial rates dependent on the nature of the dispersant, while crystalline GaQ3 dissolves only slowly without an initial dissolution peak.

Kinetic solubility curves were also determined for stressed and unstressed samples at each GaQ3:polymer

The invention claimed is:

1. An oral dosage formulation comprising a dispersion of tris (8-quinolinolato) gallium (III) (GaQ3) in amorphous or nanoparticulate form dispersed in a dispersant, and wherein the dispersion of amorphous or nanoparticulate GaQ3 in said dispersant is protected by an enteric or delayed release coating.

2. The formulation of claim 1 which is prepared by a process comprising either:
converting GaQ3 to an amorphous state in the presence of said dispersant wherein both GaQ3 and dispersant are dissolved in a solvent and evaporating the solvent to obtain an amorphous dispersion; or
suspending a nanoparticulate form in said dispersant dissolved in a solvent and evaporating the solvent to obtain said nanoparticulate surrounded by a dispersant layer.

3. The formulation of claim 2, wherein the GaQ3 is amorphous and the GaQ3 and dispersant are dissolved and spray-dried together.

4. The formulation of claim 1, wherein the weight ratio of GaQ3:dispersant is between 9:1 and 1:9.

5. The formulation of claim 1, wherein the dispersant comprises a methacrylic acid: methacrylate copolymer.

6. The formulation of claim 1, wherein the enteric or delayed release coating comprises a methacrylic acid: methacrylate copolymer.

7. The formulation of claim 1, wherein said GaQ3 is amorphous tris (8-quinolinolato) gallium (III) in a 1:1 wt/wt dispersion with Eudragit L-100 and has the powder X-ray diffraction pattern (XRD) shown in FIG. 1, curve A.

8. The formulation of claim 1, wherein said GaQ3 exhibits an immediate peak of dissolution when mixed with aqueous medium.

9. The formulation of claim 1, wherein said GaQ3 maintains its amorphous or nano-crystalline state when exposed to water vapor or to 75% relative humidity.

10. The formulation of claim 1, which, when administered to dogs at a dose of GaQ3 of 10 mg/kg, provides an AUC in plasma at least 200 times the AUC in plasma of dogs administered 10 mg/kg of crystalline GaQ3; or
when administered to dogs at a dose of GaQ3 of 10 mg/kg, provides a Cmax in plasma of at least 2336 ng/ml; or
when administered to dogs at a dose of GaQ3 of 10 mg/kg, provides an AUC in plasma of at least 60546 ng*hr/ml; or
when administered to fasted female dogs at a dose of GaQ3 of 1 mg/kg, provides an AUC in plasma of at least 4381 ng*hr/ml; or
when administered to fasted male dogs at a dose of GaQ3 of 1 mg/kg, provides an AUC in plasma of at least 4227 ng*hr/ml; or
when administered to fasted female dogs at a dose of GaQ3 of 1 mg/kg, provides a Cmax in plasma of at least 330 ng/ml; or
when administered to fasted male dogs at a dose of GaQ3 of 1 mg/kg, provides a Cmax in plasma of at least 310 ng/ml.

11. A method to administer a gallium complex to a subject which comprises administering to said subject the formulation of claim 1.

12. The method of claim 11, wherein the subject is human or a laboratory animal model.

13. The method of claim 11, wherein the subject requires treatment for cancer.

14. A method to prepare the formulation of claim 1 which method comprises
converting GaQ3 to an amorphous state in the presence of said dispersant wherein both GaQ3 and dispersant are dissolved in a solvent and evaporating the solvent to obtain an amorphous dispersion; or
suspending a nanoparticulate form in said dispersant dissolved in a solvent and evaporating the solvent to obtain said nanoparticulate surrounded by a dispersant layer.

* * * * *